(12) United States Patent
Glick et al.

(10) Patent No.: US 7,858,569 B2
(45) Date of Patent: *Dec. 28, 2010

(54) ANTIBACTERIAL COMPOSITIONS AND METHOD OF USING SAME

(75) Inventors: Francine Glick, Livingston, NJ (US); Eugene Puchalski, Jr., Jersey City, NJ (US); Annette Joubert, Whippany, NJ (US)

(73) Assignee: Water Journey Ltd., Livingston, NJ (US)

( * ) Notice: Subject to any disclaimer, the term of this patent is extended or adjusted under 35 U.S.C. 154(b) by 302 days.

This patent is subject to a terminal disclaimer.

(21) Appl. No.: 11/093,414

(22) Filed: Mar. 30, 2005

(65) Prior Publication Data

US 2005/0169880 A1 Aug. 4, 2005

Related U.S. Application Data

(62) Division of application No. 09/699,774, filed on Oct. 30, 2000, now Pat. No. 6,927,197.

(60) Provisional application No. 60/163,982, filed on Nov. 8, 1999.

(51) Int. Cl.
*A61K 8/18* (2006.01)

(52) U.S. Cl. .................. 510/131; 510/130; 510/138; 510/159; 510/500; 510/505; 424/401; 424/405; 514/156; 514/162

(58) Field of Classification Search .......... 510/131, 510/130, 138, 159, 500, 505; 252/380, 756, 252/8.61; 424/405, 401; 514/156, 162
See application file for complete search history.

(56) References Cited

U.S. PATENT DOCUMENTS

| | | | | |
|---|---|---|---|---|
| 4,732,797 A * | 3/1988 | Johnson et al. | | 428/74 |
| 5,541,233 A * | 7/1996 | Roenigk | | 521/54 |
| 5,614,201 A | 3/1997 | Slavtcheff et al. | | |
| 5,681,802 A | 10/1997 | Fujiwara et al. | | |
| 5,696,046 A * | 12/1997 | Green | | 502/161 |
| 5,859,190 A * | 1/1999 | Meyer et al. | | 530/331 |
| 5,914,300 A | 6/1999 | Fujiwara et al. | | |
| 5,942,232 A * | 8/1999 | Costa | | 424/733 |
| 6,080,707 A | 6/2000 | Glenn et al. | | |
| 6,153,208 A | 11/2000 | McAtee et al. | | |
| 6,190,678 B1 | 2/2001 | Hasenoehrl et al. | | |
| 6,294,186 B1 * | 9/2001 | Beerse et al. | | 424/405 |
| 6,333,039 B1 | 12/2001 | Fendler et al. | | |
| 6,338,855 B1 | 1/2002 | Albacarys et al. | | |
| 6,365,200 B1 | 4/2002 | Birnholz et al. | | |
| 6,710,022 B1 | 3/2004 | Kwetkat et al. | | |
| 6,927,197 B1 * | 8/2005 | Glick et al. | | 510/131 |
| 7,341,674 B1 * | 3/2008 | Trinh et al. | | 252/8.61 |

* cited by examiner

*Primary Examiner*—Vasu Jagannathan
*Assistant Examiner*—Tri V Nguyen
(74) *Attorney, Agent, or Firm*—Lerner, David, Littenberg, Krumholz & Mentlik, LLP

(57) ABSTRACT

Antibacterial solution useful as a cleaning agent suitable for cutaneous use by humans or otherwise which is aqueous based, free of alcohol and surfactants and having a quaternary ammonium compound as its principal antimicrobial agent, a number of moisturizing agents and DMDM Hydantoin serving at least as a preservative.

27 Claims, No Drawings

ANTIBACTERIAL COMPOSITIONS AND METHOD OF USING SAME

RELATED APPLICATIONS

This application is a divisional of U.S. application Ser. No. 09/699,774 filed on Oct. 30, 2000, and also claims benefit of U.S. Provisional Patent Application No. 60/163,982 filed Nov. 8, 1999, the disclosure of which is hereby incorporated by reference herein.

FIELD OF THE INVENTION

This invention relates to antibacterial solutions useful as a cleansing agent suitable for cutaneous use by humans, as well as for application to non-absorbent equipment surfaces. The solution is designed to be applied directly to the surface which is to be cleaned without any need to rinse it off. The antimicrobial solution is aqueous based, is free of surfactants, alcohol or other skin-drying or odor producing ingredients and contains a quaternary ammonium compound as its principal antimicrobial agent. The solution also contains a combination of moisturizing agents such as extracts of aloe vera, lavender and chamomile. Additionally, DMDM hydantoin is blended into the solution and acts at least as a preservative.

BACKGROUND

There are a large number of formulations for antibacterial cleansing solutions which include the quaternary ammonium compound Benzalkonium Chloride. At least some of the benzalkonium chloride formulations also make use of DMDM Hydantoin (e.g. "Glydant XL 1000") as a preservative in the solution (see for example, U.S. Pat. No. 5,914,300, granted Jun. 22, 1999 in the names of Fujiwara et al., which is assigned to Lever Brothers Company).

Although the antibacterial effect of benzalkonium chloride has been recognized by workers in this field, nevertheless, it is customary to include materials in the cleaning solution such as surfactants and/or alcohols to provide a significant degree of the desired cleansing and antibacterial effects. In addition, in most instances, fragrances are added to the composition as well to provide supposedly desirable characteristics to the product.

It has been found, however, that a highly effective and desirable antibacterial cleansing solution which does not require rinsing preferably is formulated free of fragrance, alcohol and surfactants. The undesirable drying effect of alcohol on the skin is avoided while, at the same time, providing an aqueous-based, substantially residue-free, odor-free, effective antibacterial cleansing solution. The solution may be applied as a spray or liquid or it may be saturated in a medium such as an absorbent gauze or other fabric (e.g. a towelette) which is used as a "wipe" on the skin or surface to be cleaned.

An exemplary formulation includes a water phase, a principal active phase, a preservative phase which also exhibits antibacterial effects and a moisturizing phase.

STATEMENT OF INVENTION

It is an object of the present invention to provide a novel, effective anti-bacterial cleansing solution containing only ingredients which are specifically selected as non-irritating, non-drying and beneficial to the skin. At the same time, it has been found that such a cleansing solution can be formulated so as to be an effective anti-bacterial cleanser for non-porous equipment and other surfaces such as may be encountered in environments such as medical treatment, food handling or otherwise, where the presence of bacteria would be a concern.

With these objectives in mind, an effective anti-bacterial cleaning solution has been developed which is alcohol-free, surfactant-free and odor-free and comprises a quaternary ammonium compound in aqueous solution as its principal antimicrobial agent. The solution also contains a combination of moisturizing agents such as extracts of aloe vera, lavender and chamomile. Additionally, DMDM hydantoin is blended into the solution and acts at least as a preservative.

Certain preservatives known to be useful in liquid skin cleansers have been described as effective as preservatives because they exhibit antibacterial (and antifungal) effects themselves. It is believed that the preservative DMDM Hydantoin is one such preservative which not only provides an antibacterial effect itself but, under appropriate conditions, enhances the antibacterial effect of the principal antibacterial agent, benzalkonium chloride, when the two are combined in aqueous solution as described herein.

The principal antibacterial agent (benzalkonium chloride) can be present at a level of from about 0.1% to about 5% by weight, typically from about 0.5% to about 1.5%. The level is selected to provide the desired level of antibacterial activity and can be modified within the indicated ranges as desired.

The stated moisturizing agents (extracts of aloe vera, chamomile and lavender) can be present at a level of about 0.1% to about 5% by weight as a group. The principal preservative compound (DMDM Hydantoin) can be present at a level of about 0.1% to about 2% by weight. The remainder of the solution is made up of sterile water.

As a general proposition, a suitable antibacterial cleansing solution should be stable and should not deteriorate over a period of time under normal anticipated storage conditions. Further desirable attributes are that the solution should be relatively free of constituents which sensitize or irritate human skin. While a large percentage of the solution constituents are relatively inactive or inert, and serve mainly to carry or permit spreading the active ingredients, it is desirable that appropriate moisturizing or hydrating ingredients be present in order to facilitate penetration of the solution, at least to some extent, into the upper skin layer. To that end, the indicated moisturizing agents are included.

While the invention will be described in connection with a particular preferred embodiment as set forth hereinafter, it should be recognized that various modifications as may be apparent to persons skilled in the art also may be made without departing from the invention.

DETAILED DESCRIPTION

In its principal application, the inventive formulation is intended to be applied either directly or indirectly to the skin. Where a spray applicator is used, the solution is sprayed onto each hand (or skin surface which is to be cleansed) and thereafter the skin is hand rubbed gently until it is dry. Where a towelette soaked with the anti-bacterial solution is employed, the towelette is rubbed over the surface to be cleansed and transfers the solution to the surface, where it is allowed to dry in situ. The presence of the moisturizing agents, along with the absence of other objectionable residues or odors, leaves the skin clean, disinfected and pleasing to the touch.

The cleansing solution according to the present invention has been tested on humans and has been found to be non-irritating and effective as desired. The results of tests are set forth below.

Irritation and Sensitization Tests

Fifty-five subjects, male and female, ranging in age from 18 to 76 years, were selected for this evaluation. Fifty subjects completed this study. The remaining subjects discontinued their participation for various reasons unrelated to the study or the material tested. The subjects were selected on the basis, among other things, of the absence of any visible skin disease which might be confused with skin reactions from the test material, as well as avoidance of use of topical or systemic steroids and/or antihistamines for several days prior to study initiation.

The upper back between the scapulae served as the test area. Prior to the initiation of this study, towelette material was cut into 1"×¾ pieces. These samples were then placed over the gauze portion of an adhesive dressing and moistened with approximately 0.2 ml of test solution. When applied to the test site, this patch formed a semi-occlusive patch.

This procedure was followed three times per week: Monday, Wednesday and Friday, for a total of ten applications. If a participant was unable to report for an assigned test day, one makeup day was permitted. The test site was marked to ensure the continuity of patch application. Participants were instructed to remove the patch after 24 hours. The site was evaluated just prior to reapplication.

If a test site exhibited a moderate (2+) reaction (see below for key) during the Induction Phase, application would be moved to an adjacent area. Applications would be discontinued for the remainder of this test phase, if a moderate (2+) reaction was observed on this new test site. Applications would also be discontinued if a marked (3+) reaction was noted.

Rest periods consisted of twenty-four hours following each Tuesday and Thursday removal, and forty-eight hours following each Saturday removal. At the conclusion of a rest period of approximately fourteen days following the tenth application, a challenge patch was applied to the original site and to a virgin site. These sites were evaluated at twenty-four and forty-eight hours after application. The volar forearm served as the virgin test site.

Evaluation Key
0—No visible reaction
1+—Mild erythema
2+—Well-defined erythema
3+—Erythema and edema
4+—Erythema and edema with vesiculation and ulceration

| | INDIVIDUAL TEST RESULTS | | | | | | | | | | | | | |
|---|---|---|---|---|---|---|---|---|---|---|---|---|---|---|
| | INDUCTION PHASE | | | | | | | | | | | Original Site | | Virgin Site | |
| Su No | 1 | 2 | 3 | 4 | 5 | 6 | 7 | 8 | 9 | 10 | 24 | 48 | 24 | 48 |
| 1 | 0 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 | 0 |
| 3 | 0 | 0 | 0 | 0 | T* | | DID NOT COMPLETE STUDY | | | | | | | |
| 4 | 0 | 0 | 0 | 0 | 0 | 0 | 0 | 0 | 0 | 0 | 0 | 0 | 4 | 0 |
| 5 | 0 | 0 | 0 | 0 | 0 | 00 | 0 | 0 | 0 | 0 | 0 | 0 | 5 | 0 |
| 6 | 0 | 0 | 0 | 0 | 0 | 0 | 0 | 0 | 0 | 0 | 0 | 0 | 6 | 0 |
| 7 | 0 | 0 | 0 | 0 | 0 | 0 | 0 | 0 | 0 | 0 | 0 | 0 | 7 | 0 |
| 8 | 0 | | 0 | 0 | 0 | 0 | 0 | 0 | 0 | 0 | 0 | 0 | 8 | 0 |
| 9 | 0 | 0 | 0 | 0 | 0 | 0 | 0 | 0 | 0 | 0 | 0 | 0 | 9 | 0 |
| 10 | 0 | 0 | 0 | 0 | 0 | 0 | 0 | 0 | 0 | 0 | 0 | 0 | 10 | 0 |
| 11 | 0 | 0 | 0 | 0 | 0 | 0 | 0 | 0 | 0 | 0 | 0 | 0 | 11 | 0 |
| 12 | 0 | 0 | 0 | 0 | 00 | 0 | 0 | 0 | 0 | 0 | 0 | 0 | 12 | 0 |
| 13 | 0 | 0 | 0 | 0 | 0 | 0 | 0 | 0 | 0 | 0 | 0 | 0 | 13 | 0 |
| 14 | | | | | DID NOT COMPLETE STUDY | | | | | | | | | |
| 15 | 0 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | 0 | 0 | 0 | 0 |
| 18 | 0 | 0 | 0 | 0 | 0 | 0 | 0 | 0 | 0 | 0 | 0 | 0 | 0 | 0 |
| 19 | 0 | 0 | 0 | 0 | 0 | 0 | 0 | 0 | 0 | 0 | 0 | 0 | 0 | 0 |
| 20 | 0 | 0 | 0 | 0 | 0 | 0 | 0 | 0 | 0 | 0 | 0 | 0 | 0 | 0 |
| 21 | 0 | 0 | 0 | 0 | 0 | 0 | 0 | 0 | 0 | 0 | 0 | 0 | 0 | 0 |
| 22 | 0 | 0 | 0 | 0 | 0 | 0 | 0 | 0 | 0 | 0 | 0 | 0 | 0 | 0 |
| 23 | 0 | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 | 0 |
| 25 | 0 | 0 | 0 | 0 | 0 | 0 | 0 | 0 | 0 | 0 | 0 | 0 | 0 | 0 |
| 26 | 0 | 0 | 0 | 0 | 0 | 0 | 0 | 0 | 0 | 0 | 0 | 0 | 0 | 0 |
| 27 | 0 | 0 | 0 | 0 | 0 | 0 | 0 | 0 | 0 | 0 | 0 | 0 | 0 | 0 |
| 28 | 0 | 0 | 0 | 0 | 0 | 0 | 0 | 0 | 0 | 0 | 0 | 0 | 0 | 0 |
| 29 | 0 | 0 | 0 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 | 0 | 0 | 0 |
| 31 | 0 | 0 | 0 | 0 | 0 | 0 | 0 | 0 | 0 | 0 | 0 | 0 | 0 | 0 |
| 32 | 0 | 0 | 0 | 0 | 0 | 0 | 0 | 0 | 0 | 0 | 0 | 0 | 0 | 0 |
| 33 | 0 | 0 | 0 | 0 | 0 | 0 | 0 | 0 | 0 | 0 | 0 | 0 | 0 | 0 |
| 34 | 0 | 0 | 0 | 0 | 0 | 0 | 0 | 0 | 0 | 0 | 0 | 0 | 0 | 0 |
| 35 | 0 | 0 | 0 | 0 | 0 | 0 | 0 | 0 | 0 | 0 | 0 | 0 | 0 | 0 |
| 36 | 0 | 0 | 0 | 0 | 0 | 0 | 0 | 0 | 0 | 0 | 0 | 0 | 0 | 0 |
| 37 | 0 | 0 | 0 | 0 | 0 | 0 | 0m | 0 | 0 | 0 | 0 | 0 | 0 | 0 |
| 38 | 0 | | | | DID NOT COMPLETE STUDY | | | | | | | | | |
| 39 | 0 | 0 | 0 | 0 | 0 | 0 | 0 | 0 | 0 | 0 | 0 | 0 | 0 | 0 |
| 40 | 0 | | | | DID NOT COMPLETE STUDY | | | | | | | | | |
| 41 | 0 | 0 | 0 | 0 | 0 | 0 | 0 | 0 | 0 | 0 | 0 | 0 | 0 | 0 |
| 42 | 0 | 0 | 0 | 0 | 0 | 0 | 0 | 0 | 0 | 0 | 0 | 0 | 0 | 0 |
| 43 | 0 | | | | DID NOT COMPLETE STUDY | | | | | | | | | |
| 44 | 0 | 0 | 0 | 0 | 0 | 0 | 0 | 0 | 0 | 0 | 0 | 0 | 0 | 0 |
| 45 | 0 | 0 | 0 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 | 0 | 0 | 0 |
| 47 | 0 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 | 0 |
| 49 | 0 | 0 | 0 | 0 | 0 | 0 | 0 | 0 | 0 | 0 | 0 | 0 | 0 | 0 |
| 50 | 0 | 0 | 0 | 0 | 0 | 0 | 0 | 0 | 0 | 0 | 0 | 0 | 0 | 0 |
| 51 | 0 | 0 | 0 | 0 | 0 | 0 | 0 | 0 | 0 | 0 | 0 | 0 | 0 | 0 |
| 52 | 0 | 0 | 0 | 0 | 0 | 0 | 0 | 0 | 0 | 0 | 0 | 0 | 0 | 0 |
| 53 | 0 | 0 | 0 | 0 | 0 | 0 | 0 | 0 | 0 | 0 | 0 | 0 | 0 | 0 |
| 54 | 0 | 0 | 0 | 0 | 0 | 0 | 0 | 0 | 0 | 0 | 0 | 0 | 0 | 0 |
| 55 | 0 | 0 | 0 | 0 | 0 | 0 | 0 | 0 | 0 | 0 | 0 | 0 | 0 | 0 |
| 44 | 0 | 0 | 0 | 0 | 0 | 0 | 0 | 0 | 0 | 0 | 0 | 0 | 0 | 0 |
| 45 | 0 | 0 | 0 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 | 0 | 0 | 0 |
| 47 | 0 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 | 0 |
| 49 | 0 | 0 | 0 | 0 | 0 | 0 | 0 | 0 | 0 | 0 | 0 | 0 | 0 | 0 |
| 50 | 0 | 0 | 0 | 0 | 0 | 0 | 0 | 0 | 0 | 0 | 0 | 0 | 0 | 0 |
| 51 | 0 | 0 | 0 | 0 | 0 | 0 | 0 | 0 | 0 | 0 | 0 | 0 | 0 | 0 |
| 52 | 0 | 0 | 0 | 0 | 0 | 0 | 0 | 0 | 0 | 0 | 0 | 0 | 0 | 0 |
| 53 | 0 | 0 | 0 | 0 | 0 | 0 | 0 | 0 | 0 | 0 | 0 | 0 | 0 | 0 |
| 54 | 0 | 0 | 0 | 0 | 0 | 0 | 0 | 0 | 0 | 0 | 0 | 0 | 0 | 0 |
| 55 | 0 | 0 | 0 | 0 | 0 | 0 | 0 | 0 | 0 | 0 | 0 | 0 | 0 | 0 |

T = TAPE REACTION
m = ADDITIONAL MAKEUP FOR MEDICAL EMERGENCY

| SUBJECT DATA | | | |
|---|---|---|---|
| SUBJECT NUMBER | INITIALS | AGE | SEX |
| 1 | LA | 74 | F |
| 2 | JS | 24 | F |
| 3 | JM | 28 | M |
| 4 | MB | 67 | F |
| 5 | AZ | 76 | M |
| 6 | JC | 67 | F |
| 7 | RS | 64 | M |
| 8 | ST | 74 | F |

-continued

SUBJECT DATA

| SUBJECT NUMBER | INITIALS | AGE | SEX |
|---|---|---|---|
| 9 | CS | 56 | F |
| 10 | SC | 54 | F |
| 11 | CY | 75 | M |
| 12 | DR | 33 | F |
| 13 | MH | 60 | F |
| 14 | AS | 70 | F |
| 15 | AM | 65 | F |
| 16 | JM | 70 | M |
| 17 | GR | 21 | F |
| 18 | CB | 49 | F |
| 19 | SS | 62 | F |
| 20 | SS | 72 | M |
| 21 | MS | 66 | F |
| 22 | AP | 29 | F |
| 23 | TP | 73 | M |
| 24 | RL | 50 | F |
| 25 | RS | 49 | M |
| 26 | WW | 36 | M |
| 27 | SM | 32 | F |
| 28 | MS | 60 | F |
| 29 | LC | 27 | F |
| 30 | CL | 65 | F |
| 31 | GF | 65 | F |
| 32 | RG | 46 | M |
| 33 | CR | 40 | F |
| 34 | MS | 34 | F |
| 35 | AH | 38 | F |
| 36 | IB | 51 | F |
| 37 | DH | 30 | F |
| 38 | AC | 19 | F |
| 39 | TR | 18 | F |
| 40 | CS | 18 | M |
| 41 | GA | 55 | F |
| 42 | PM | 53 | F |
| 43 | DM | 26 | F |
| 44 | MF | 50 | F |
| 45 | EL | 50 | F |
| 46 | JT | 30 | F |
| 47 | AN | 74 | F |
| 48 | LS | 30 | F |
| 49 | DS | 28 | M |
| 50 |  | 66 | M |
| 51 | MM | 41 | F |
| 52 | CA | 20 | F |
| 53 | HV | 65 | F |
| 54 | GV | 70 | M |
| 55 | AS | 36 | M |

The results of the tests show negative results (no irritation or other effects) throughout the test intervals. Under the conditions of these studies, the towelette solution/material did not indicate any potential for dermal irritation and/or sensitization.

A sample of solution was submitted for microbiological evaluation and standard time kill test at 30 seconds, 1 minute and 2 minutes.

A "Time Kill Study" was conducted to determine the antibacterial activity of the sample solution after 30 seconds, 1 minute and 2 minutes contact time against Pseudomonas aeruginosa ATCC 15422, *S. aureus* ATOC 6538 and *E. coli* ATCC 8739. Results showed that the sample solution reduced bacteria count by 99.99% at 30 seconds contact time. It is typical for antimicrobial soap products to show a minimum of 99.99% reduction of the test organisms to substantiate antimicrobial claims.

| SAMPLE | CONTACT TIME | INITIAL CONCENT. IN SAMPLE | CFU'S/ML OF TEST ORG. AT T = SEC. | PERCENT REDUCTION |
|---|---|---|---|---|
| *P. aerugino*-sa ATTC 15442 | 30 Sec. | $2.7 \times 10^7$ | Less than 10 | 99.99% |
|  | 1 Min. | $2.7 \times 10^7$ | Less than 10 | 99.99% |
|  | 2 Min. | $2.7 \times 10^7$ | Less than 10 |  |
| *S. aureus* ATCC 6538 | 30 Sec. | $2.5 \times 10^7$ | Less than 10 | 99.99% |
|  | 1 Min. | $2.5 \times 10^7$ | Less than 10 | 99.99% |
|  | 2 Min. | $2.5 \times 10^7$ | Less than 10 | 99.99% |
| *E. coli* ATCC 8739 | 30 Sec. | $4.7 \times 10^7$ | Less than 10 | 99.99% |
|  | 1 Min. | $4.7 \times 10^7$ | Less than 10 | 99.99% |
|  | 2 Min. | $4.7 \times 10^7$ | Less than 10 | 99.99% |

The use of natural extracts in a water-based solution, which is fragrance, alcohol and surfactant-free, provides a desired moisturizing effect, along with the necessary antibacterial effect and the cleansing solution does not strip the skin of its natural oils.

While the invention has been described in terms of a preferred embodiment and preferred methods of use, it should be recognized that various modifications may be made within the scope of the invention which is pointed out in the following claims.

The invention claimed is:

1. A skin or surface sanitizer composition prepared from a mixture comprising:
    (A) at least one antibacterial agent consisting a quaternary ammonium compound;
    (B) a preservative;
    (C) a combination of moisturizing or hydrating agents; and
    (D) water;
provided said composition does not contain: (1) alcohol; and (2) surfactant.

2. The composition of claim 1 wherein said quaternary ammonium compound is benzalkonium chloride.

3. The composition of claim 1 wherein said preservative comprises DMDM Hydantoin.

4. The composition of claim 1 wherein said combination of moisturizing or hydrating agents comprises plant extracts.

5. The composition of claim 4 wherein said combination of moisturizing or hydrating agents include extracts selected from the group consisting of aloe vera, lavender and chamomile.

6. The composition of claim 1 wherein, based on the total weight of said composition, said antibacterial agent comprises from about 0.1 to about 5 weight percent, said preservative comprises about 0.1 to about 2 weight percent and said combination of moisturizing or hydrating agents comprises about 0.1 to about 5 total weight percent.

7. The composition of claim 2 wherein said benzalkonium chloride is present in an amount of from about 0.5 to about 1.5 weight percent of said composition.

8. The composition of claim 1 wherein said combination of moisturizing agents are selected from the group consisting of aloe vera, lavender and chamomile.

9. The composition of claim 4 wherein said antibacterial agent comprises benzalkonium chloride.

10. The composition of claim 5 wherein said combination of moisturizing agents is extracts of aloe vera and chamomile.

11. The composition of claim 1 comprising:
    (A) from about 0.1 to about 5 weight percent of at least one antibacterial agent;
    (B) about 0.1 to about 2 weight percent of a preservative;

(C) about 0.1 to about 5 total weight percent of a combination of moisturizing or hydrating agents; and
(D) water;
wherein said at least one antibacterial agent comprises benzalkonium chloride; said preservative comprises DMDM Hydantoin and said combination of moisturizing agents comprises extracts of aloe vera, lavender and chamomile.

12. A skin or surface sanitizer composition prepared from a mixture comprising:
(A) at least one antibacterial agent a quaternary ammonium compound;
(B) a preservative;
(C) a combination of moisturizing or hydrating agents; and
(D) water;
provided said composition does not contain: (1) a skin-drying ingredient; and (2) surfactant.

13. The composition of claim 12 wherein said skin-drying ingredient comprises alcohol.

14. The composition of claim 12 wherein said quaternary ammonium compound is benzalkonium chloride.

15. The composition of claim 12 wherein said preservative comprises DMDM Hydantoin.

16. The composition of claim 12 wherein said combination of moisturizing or hydrating agents comprises plant extracts.

17. The composition of claim 16 wherein said combination of moisturizing or hydrating agents include extracts selected from the group consisting of aloe vera, lavender and chamomile.

18. The composition of claim 12 wherein, based on the total weight of said composition, said antibacterial agent comprises from about 0.1 to about 5 weight percent, said preservative comprises about 0.1 to about 2 weight percent and said combination of moisturizing or hydrating agents comprises about 0.1 to about 5 total weight percent.

19. The composition of claim 14 wherein said benzalkonium chloride is present in an amount of from about 0.5 to about 1.5 weight percent of said composition.

20. The composition of claim 12 wherein said combination of moisturizing agents are selected from the group consisting of aloe vera, lavender and chamomile.

21. The composition of claim 16 wherein said antibacterial agent comprises benzalkonium chloride.

22. The composition of claim 17 wherein said combination of moisturizing agents is extracts of aloe vera and chamomile.

23. A method of cleansing an area of skin comprising applying the composition of claim 1 to said area of skin to be cleansed.

24. The method of claim 23 wherein the composition is applied to the skin of a human.

25. The method of claim 23 wherein the step of applying comprises spraying said composition on the area to be cleaned.

26. The method of claim 23 wherein the step of applying comprises wetting an absorbent medium with said composition and wiping said wet medium over said area.

27. A cleansing wipe comprising the composition according to claim 1 in combination with a medium selected from the group consisting of absorbent gauze, towelette, cloth and other fabric.

* * * * *

UNITED STATES PATENT AND TRADEMARK OFFICE
CERTIFICATE OF CORRECTION

| | | |
|---|---|---|
| PATENT NO. | : 7,858,569 B2 | Page 1 of 1 |
| APPLICATION NO. | : 11/093414 | |
| DATED | : December 28, 2010 | |
| INVENTOR(S) | : Francine Glick, Eugene Puchalski, Jr. and Annette Joubert | |

It is certified that error appears in the above-identified patent and that said Letters Patent is hereby corrected as shown below:

Column 3, line 13, "1"×3/4" should read --1" × 3/4"--.

Column 5, at Subject Data table, Subject Number 50, under "INITIALS" heading insert --PP--.

Column 6, line 31, after "consisting" insert --of--.

Column 6, line 45, "include" should read --includes--.

Column 6, line 58, "are" should read --is--.

Column 7, line 11, after "agent" insert --consisting of--.

Column 7, line 26, "include" should read --includes--.

Column 8, line 9, "are" should read --is--.

Signed and Sealed this
Twenty-first Day of February, 2012

David J. Kappos
*Director of the United States Patent and Trademark Office*